(12) United States Patent
Ward et al.

(10) Patent No.: US 6,695,860 B1
(45) Date of Patent: Feb. 24, 2004

(54) TRANSCUTANEOUS SENSOR INSERTION DEVICE

(76) Inventors: W. Kenneth Ward, Portland, OR (US); Lawrence B. Jansen, Portland, OR (US)

( * ) Notice: Subject to any disclaimer, the term of this patent is extended or adjusted under 35 U.S.C. 154(b) by 250 days.

(21) Appl. No.: 09/711,690

(22) Filed: Nov. 13, 2000

(51) Int. Cl.$^7$ .............................................. A61B 17/34
(52) U.S. Cl. ........................................ 606/185; 600/505
(58) Field of Search ................................ 606/184, 185, 606/167; 604/55, 61, 62, 160, 180, 164; 600/500, 505

(56) References Cited

U.S. PATENT DOCUMENTS

| | | | |
|---|---|---|---|
| 4,671,288 A | * 6/1987 | Gough | 204/403.1 |
| 4,777,953 A | * 10/1988 | Ash et al. | 600/347 |
| 4,816,021 A | 3/1989 | Johnson | 604/110 |
| 4,838,877 A | 6/1989 | Massau | 604/272 |
| 4,955,863 A | 9/1990 | Walker et al. | 604/165 |
| 4,976,704 A | 12/1990 | McLees | 604/265 |
| 5,083,573 A | * 1/1992 | Arms | 600/587 |
| 5,108,380 A | 4/1992 | Herlitze et al. | 604/283 |
| 5,250,066 A | 10/1993 | Lambert | 606/181 |
| 5,390,671 A | 2/1995 | Lord et al. | 128/635 |
| 5,441,489 A | 8/1995 | Utsumi et al. | 604/280 |
| 5,520,666 A | 5/1996 | Choudhury et al. | 604/283 |
| 5,586,553 A | 12/1996 | Halili et al. | 128/635 |
| 5,634,913 A | 6/1997 | Stinger | 604/272 |
| 5,762,630 A | 6/1998 | Bley et al. | 604/164 |
| 5,779,665 A | 7/1998 | Mastrototaro et al. | 605/51 |
| 5,885,257 A | 3/1999 | Badger | 604/195 |
| 5,899,887 A | 5/1999 | Liu | 604/195 |
| 5,987,352 A | * 11/1999 | Klein et al. | 600/509 |

* cited by examiner

*Primary Examiner*—Danny Worrell

(57) ABSTRACT

An insertion device that includes an insertable portion adapted to be inserted into and retained in an animal body and an ex vivo portion that is adapted to be worn while the insertable portion remains inserted. The device further includes a trocar that is adapted to insert the insertable portion into the animal body. In addition, a cavity in the ex vivo portion is adapted to accept and retain the trocar after the insertable portion is inserted and a force application device is adapted to withdraw the trocar from the animal body and place it in the cavity.

11 Claims, 4 Drawing Sheets

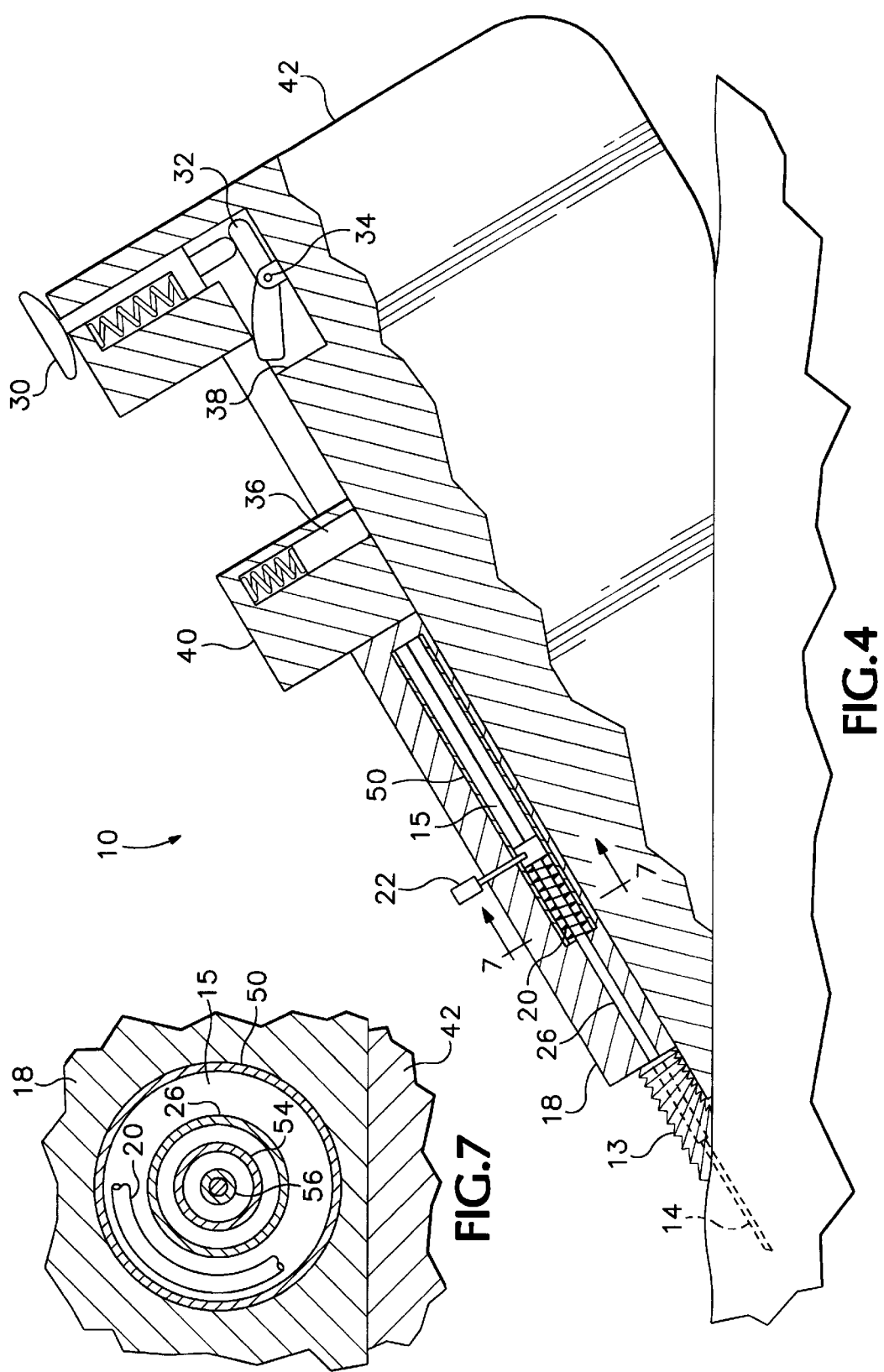

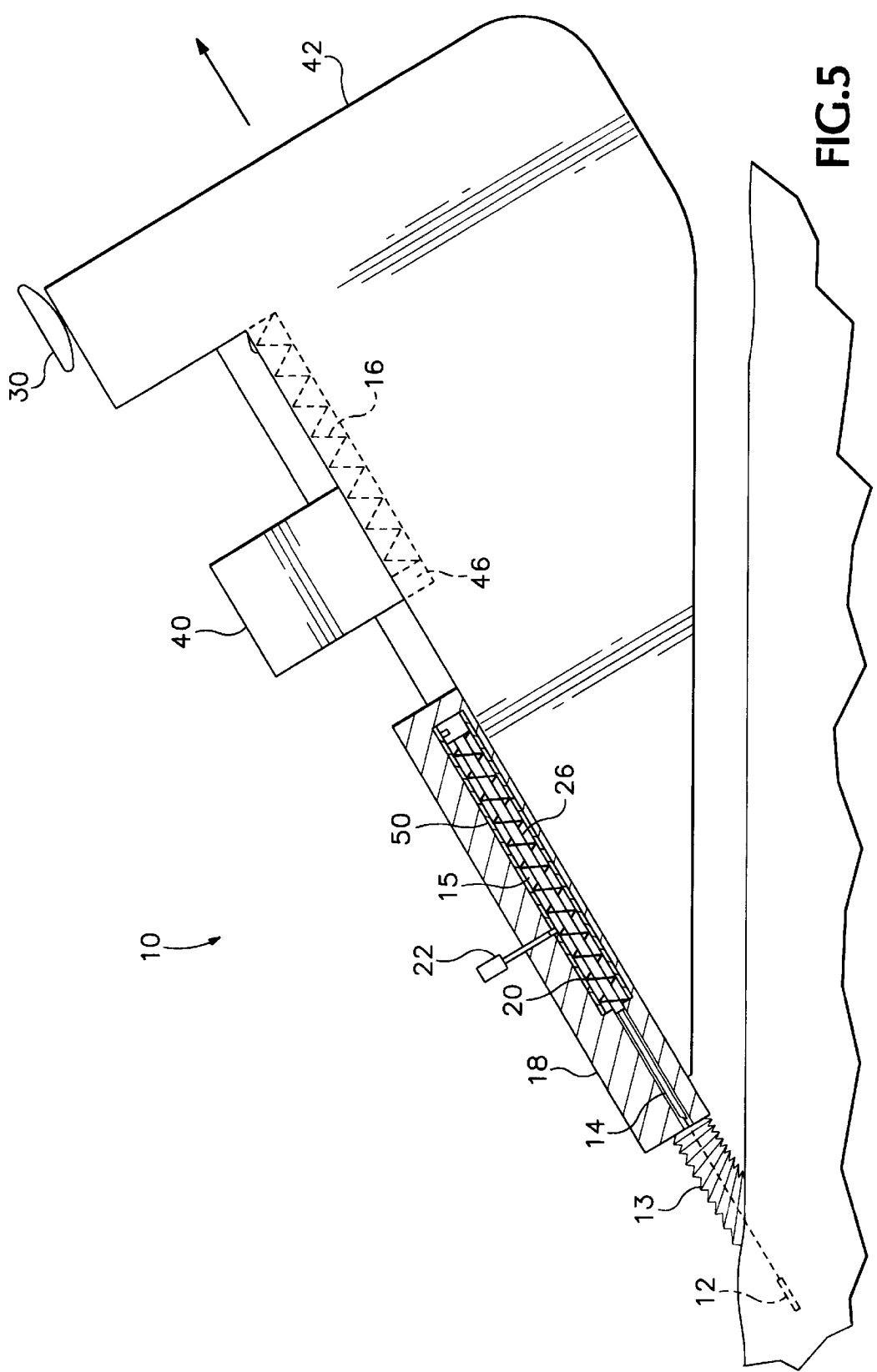

TRANSCUTANEOUS SENSOR INSERTION DEVICE

STATEMENT OF GOVERNMENT SUPPORT

The invention which is the subject of this application was funded in part by The Center for Disease Control Grant No.: RO CCR017796. The government retains certain rights in the invention.

BACKGROUND OF THE INVENTION

The present invention has to do with an insertion device for a transcutaneous sensor. The insertion of a transcutaneous sensor has long proved a difficult problem. It is advantageous that a transcutaneous sensor be made as thin as possible so that the disruption to the skin is minimized. With current materials, however, it is difficult to impossible for such a thin device to be made strong enough to breach the skin. A hypodermic needle would be a good type of introduction device or trocar (medical breaching device), but if the transcutaneous sensor is threaded through the hypodermic needle, then the removal of the transcutaneous sensor from within the hypodermic needle presents a real difficulty. There is a teaching of the use of a slotted needle to introduce the sensor and then permit the disengagement of the sensor and introduction device. Nevertheless, there is an unfilled need for an alternative method of introducing a transcutaneous sensor into a patient or test subject. It would be desirable for such a method to use a standard, and therefore widely available, hypodermic needle as a trocar.

SUMMARY

An insertion device includes an insertable portion adapted to be inserted into and retained in an animal body and an ex vivo portion that is adapted to be worn while the insertable portion remains inserted. The device further includes a trocar that is adapted to insert the insertable portion into the animal body. In addition, a cavity in the ex vivo portion is adapted to accept and retain the trocar after the insertable portion is inserted and a force application device is adapted to withdraw the trocar from the animal body and place it in the cavity.

An insertion device is adapted to automatically insert a biodevice into an animal body. The device includes a guide portion having first and second major exterior surfaces set at an acute angle to each other and a trocar set to releasably slide along the first major surface. In addition, a force application assembly is adapted to release the trocar and force it to slide along the first major surface.

The foregoing and other objectives, features and advantages of the invention will be more readily understood upon consideration of the following detailed description of the preferred embodiment(s), taken in conjunction with the accompanying drawings.

BRIEF DESCRIPTION OF THE DRAWINGS

FIG. 3 is a cross-sectional view of the insertion device of FIG. 1, taken along line 3—3 of FIG. 1.

FIG. 4 is a cross-sectional view of the insertion device of FIG. 1, but in its insertion state, taken along line 3—3 of FIG. 1.

FIG. 5 is a cross-sectional view of the insertion device of FIG. 1, but in its trocar withdrawn state, taken along line 3—3 of FIG. 1.

FIG. 6 is a side view of the sensor and base unit portions of the insertion device of FIG. 1, shown after the insertion operation is fully completed.

FIG. 7 is a cross-sectional view of the insertion device of FIG. 4, taken along line 7–7 of FIG. 4.

DETAILED DESCRIPTION OF THE PREFERRED EMBODIMENT

Figure 1:
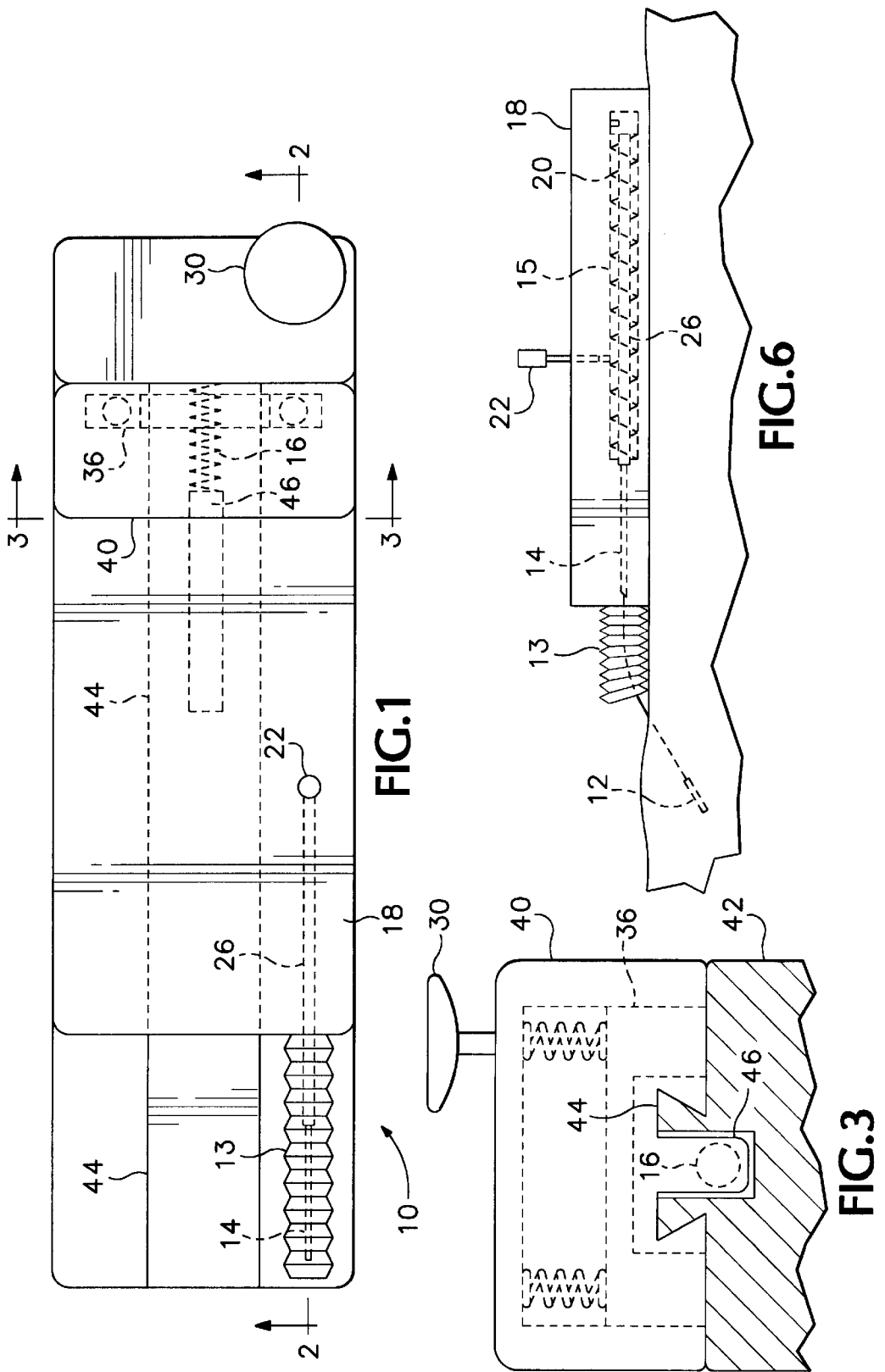
FIG. 1 is a plan view of an insertion device according to the present invention, in its unactuated state.

FIG. 1 is a side cross-sectional view of a transcutaneous sensor insertion device 10 according to the present invention. To introduce a sensor 12 (FIG. 4), a trocar in the form of a hypodermic needle 14, which is kept in a void space 15 until needed, is automatically pushed through the skin by a pair of springs 16. Subsequently, needle 14 is retracted into a cavity in a sensor base unit 18 by a spring 20, which is released when a pin 22 is pulled upwardly by a user. Collectively, spring 20 and pin 22 can be termed a force application device. Sensor base unit 18 remains fastened to the skin of the patient by means of a strap (not shown) or other attachment device for as long as the sensor 12 is in use. Sensor base unit may additionally include a display window, controls or a transmission device for making available the readings from the sensor 12, either locally or remotely.

Figure 2:
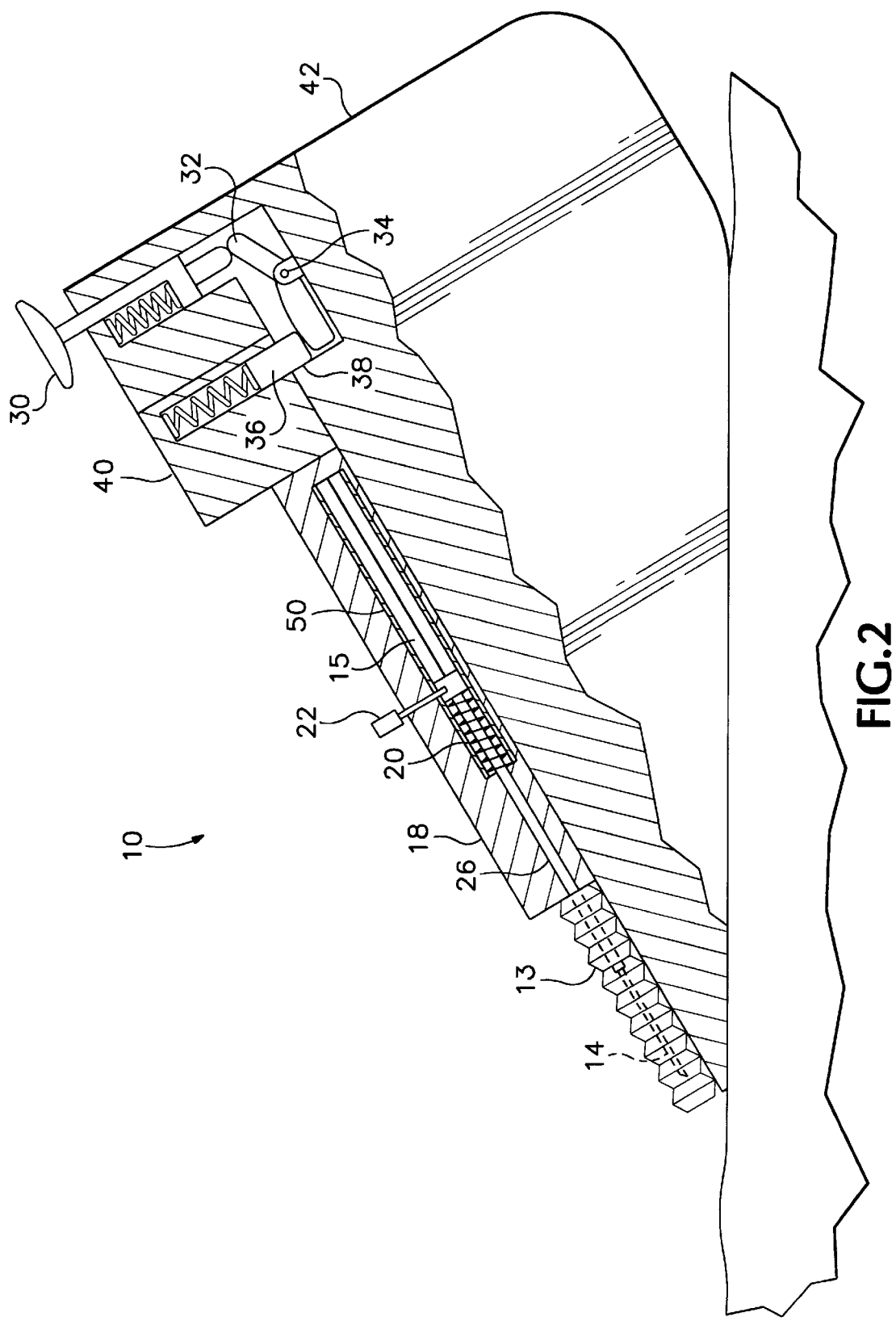
FIG. 2 is a cross-sectional view of the insertion device of FIG. 1, taken along line 2—2 of FIG. 1.

Referring to FIGS. 2, 4 and 5, the mechanism for releasing springs 16, to push needle 14 into the body, includes a plunger 30, which may be depressed to rotate a lever 32 about a pivot 34. When this operation is performed, lever 32 presses up against a spring loaded pin 36, which, when it clears a trip surface 38 permits both a slide block 40 and the sensor base unit 18 to be pulled forward by springs 16, thereby pushing needle 14 into the tissue of the patient. A disposable guide housing 42 supports the slide block 40 and the sensor base unit 18 at an advantageous angle with respect to the surface of the patient's body. Plunger 30, lever 32 spring loaded pin 36 and surface 38 may collectively be termed the trocar catch release mechanism and this plus springs 16 may be termed a force application assembly.

After being inserted, needle 14 may be automatically removed by drawing upwardly on pin 22 to release spring 20. The contraction of spring 20 causes needle 14 to be retracted into the void space 15 in sensor base unit 18. Needle 14 remains in void space 15 until the sensor 12 is removed from the patient and it and base unit 18 are disposed.

The terms and expressions which have been employed in the foregoing specification are used as terms of description and not of limitation, and there is no intention, in the use of such terms and expressions, of excluding equivalents of the features shown and described or portions thereof, it being recognized that the scope of the invention is defined and limited only by the claims which follow. The term "animal" as used in this application includes human beings.

What is claimed is:

1. An insertion device including an insertable portion adapted to be inserted into and retained in an animal body and an ex vivo portion that is adapted to be worn while said insertable portion remains inserted, said device comprising:

(a) a trocar adapted to insert said insertable portion into said animal body;

(b) a cavity in said ex vivo portion adapted to accept, retain and substantially enclose said trocar subsequent to said insertable portion being inserted; and (c) a force application device adapted to withdraw said trocar from said animal body and place it in said cavity.

2. The device of claim 1 wherein said trocar is in the form of a hypodermic needle.

3. The device of claim 1 wherein said insertable portion is a sensor.

4. The device of claim 3 wherein said sensor is a glucose sensor.

5. The device of claim 1 further including an additional force application device adapted to push said trocar into said animal body.

6. An insertion device adapted to automatically insert a biodevice into a human or animal body, said device comprising:
   (a) a guide portion having first and second major exterior nonparallel surfaces;
   (b) a trocar set to releasably slide along said first major surface; and
   (c) an energy storage and force application assembly adapted to release said trocar and release stored energy to force said trocar to slide along said first major surface and causing said trocar to breach the skin of said animal body if said second major exterior surface is being held against said skin.

7. The device of claim 6 wherein said force application assembly includes springs and a trocar catch release mechanism, said springs being adapted to push said trocar along said first major surface when said trocar catch release mechanism is actuated.

8. The device of claim 7 wherein said trocar has a sharp point and is substantially enclosed in a cavity prior to being pushed into said animal body by said energy storage and force application device and which thereby never exposes any user to said sharp point of said trocar.

9. The device of claim 1 wherein said force application device is also an energy storage device and wherein energy is released from said energy storage device to withdraw said trocar from said animal body and place it in said cavity.

10. The device of claim 9 wherein said energy storage and force application device includes a spring adapted to pull said trocar from said body.

11. The device of claim 10 wherein said energy storage and force application device includes a pin that is adapted to release said spring when manipulated in a predetermined manner.

* * * * *

UNITED STATES PATENT AND TRADEMARK OFFICE
CERTIFICATE OF CORRECTION

PATENT NO. : 6,695,860 B1
DATED : February 24, 2004
INVENTOR(S) : W. Kenneth Ward and Lawrence B. Jansen It is certified that error appears in the above-identified patent and that said Letters Patent is hereby corrected as shown below:

Title page,
Insert item:
-- [73]   Assignee:  iSense Corp. Portland, Oregon --.

Signed and Sealed this

Eleventh Day of May, 2004

JON W. DUDAS
*Acting Director of the United States Patent and Trademark Office*